(12) United States Patent
Bunton et al.

(10) Patent No.: US 7,652,269 B2
(45) Date of Patent: Jan. 26, 2010

(54) LASER ATOM PROBE METHODS

(75) Inventors: Joseph Hale Bunton, Madison, WI (US); Jesse D. Olson, Madison, WI (US)

(73) Assignee: Imago Scientific Instruments Corporation, Madison, WI (US)

( * ) Notice: Subject to any disclaimer, the term of this patent is extended or adjusted under 35 U.S.C. 154(b) by 589 days.

(21) Appl. No.: 11/597,080

(22) PCT Filed: Aug. 19, 2004

(86) PCT No.: PCT/US2004/026823

§ 371 (c)(1),
(2), (4) Date: Nov. 17, 2006

(87) PCT Pub. No.: WO2005/122210

PCT Pub. Date: Dec. 22, 2005

(65) Prior Publication Data

US 2007/0181826 A1  Aug. 9, 2007

Related U.S. Application Data

(60) Provisional application No. 60/576,557, filed on Jun. 3, 2004.

(51) Int. Cl.
    G01B 5/28 (2006.01)
    H01J 37/285 (2006.01)
    H01J 49/00 (2006.01)
(52) U.S. Cl. ............... 250/491.1; 250/492.1; 250/281; 250/282; 250/306; 250/307; 250/309; 250/310

(58) Field of Classification Search .......... 250/281, 250/282, 287, 288, 306, 307, 309, 310, 423 F, 250/423 R, 491.1, 492.1
See application file for complete search history.

(56) References Cited

U.S. PATENT DOCUMENTS

| | | | |
|---|---|---|---|
| 6,580,069 B1 | 6/2003 | Cerezo et al. | |
| 6,875,981 B2 * | 4/2005 | Nishikawa | 850/26 |
| 2003/0154773 A1 * | 8/2003 | Nishikawa | 73/105 |
| 2003/0168595 A1 * | 9/2003 | Danilatos | 250/310 |
| 2004/0109532 A1 * | 6/2004 | Ford et al. | 378/57 |
| 2006/0060783 A1 * | 3/2006 | Armit | 250/310 |
| 2007/0181826 A1 * | 8/2007 | Bunton et al. | 250/491.1 |
| 2007/0205358 A1 * | 9/2007 | Bunton et al. | 250/282 |

* cited by examiner

Primary Examiner—Bernard E Souw
(74) Attorney, Agent, or Firm—Perkins Coie LLP

(57) ABSTRACT

A laser atom probe (100) situates a counter electrode between a specimen mount and a detector (106), and provides a laser (116) having its beam (122) aligned to illuminate the specimen (104) through the aperture (110) of the counter electrode (108). The detector, specimen mount (102), and/or the counter electrode may be charged to some boost voltage and then be pulsed to bring the specimen to ionization. The timing of the laser pulses may be used to determine ion departure and arrival times allowing determination of the mass-to-charge ratios of the ions, thus their identities. Automated alignment methods are described wherein the laser is automatically directed to areas of interest.

42 Claims, 7 Drawing Sheets

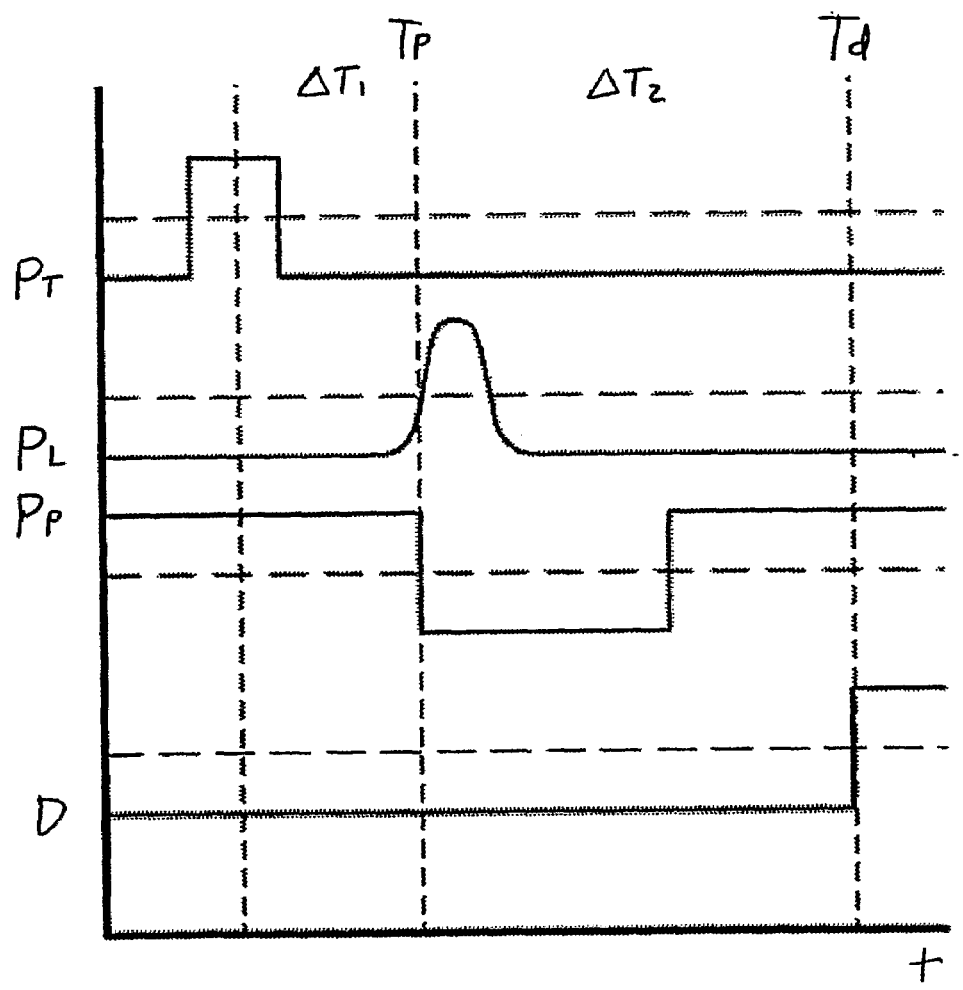

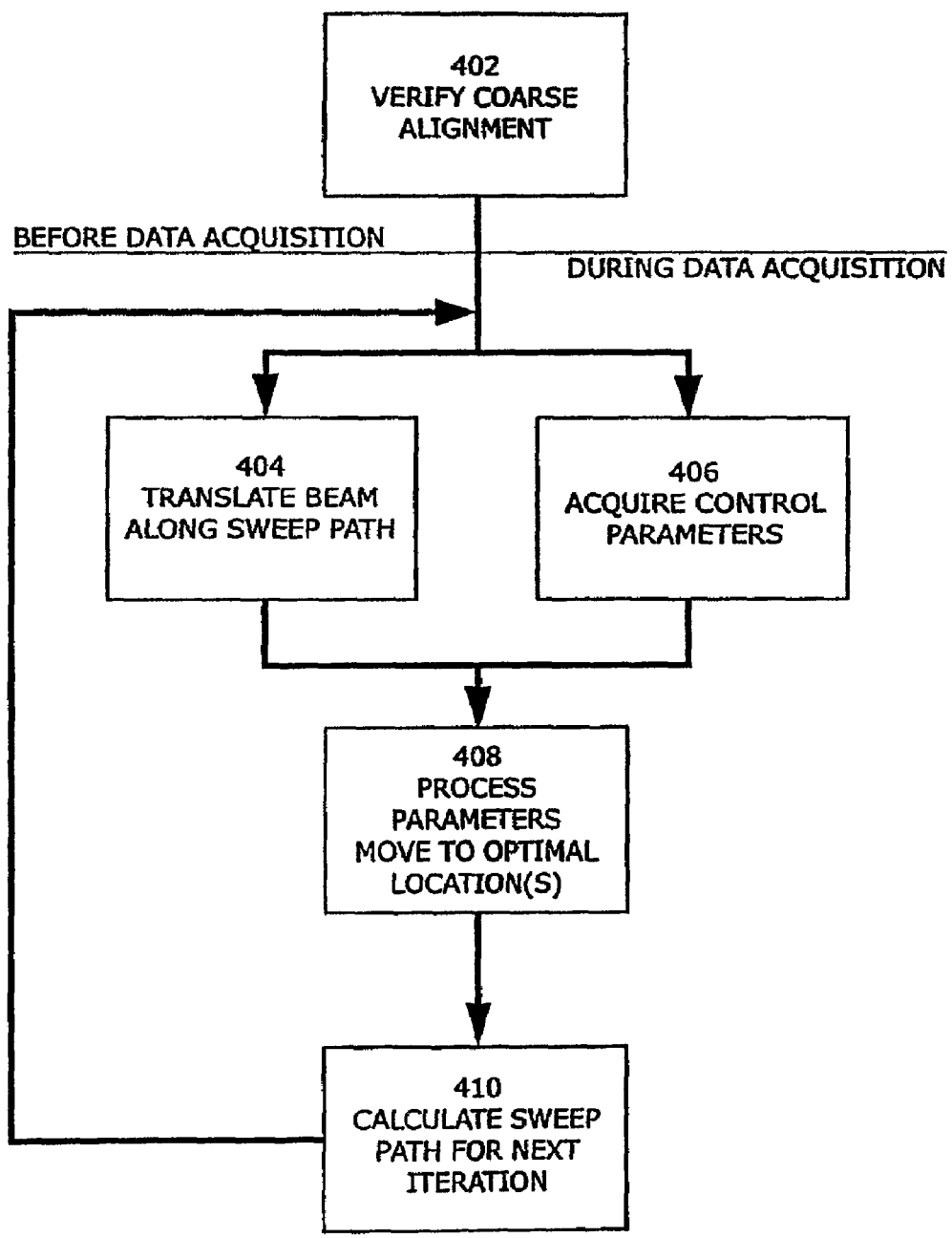

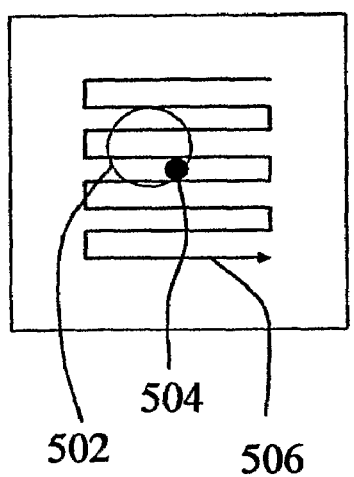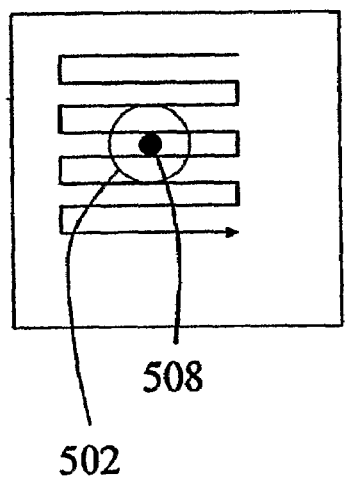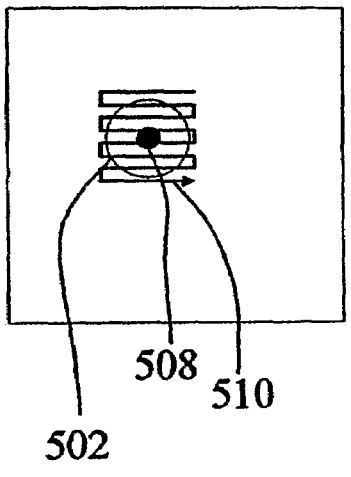

LASER ATOM PROBE METHODS

CROSS-REFERENCE TO RELATED APPLICATIONS

This application is a U.S. National Phase application of International Patent Application No. PCT/US2004/026823, filed Aug. 19, 2004, which claims the benefit of U.S. Provisional Patent Application No. 60/576,557, filed Jun. 3, 2004, each of which is incorporated herein by reference in its entirety. This application also claims the benefit of pending U.S. patent application Ser. No. 10/592.661 filed Sep. 12. 2006, which is incorporated herein by reference in its entirety.

FIELD OF THE INVENTION

This document concerns an invention relating generally to atom probes, also known as atom probe microscopes.

BACKGROUND OF THE INVENTION

The atom probe (also referred to as an atom probe microscope) is a device which allows specimens to be analyzed on an atomic level. A basic version of a conventional atom probe might take the following form. A specimen mount is spaced from a detector, generally a microchannel plate and delay line anode. A specimen is situated in the specimen mount, and the charge (voltage) of the specimen holder is adapted versus the charge of the detector such that atoms on the specimen's surface ionize and "evaporate" from the specimen's surface, and travel to the detector. Generally, the voltage of the specimen is pulsed so that the pulses trigger evaporation events with the timing of the pulses, thereby allowing at least a rough determination of the time of evaporation. The specimen's atoms tend to ionize in accordance with their distance from the detector (i.e., atoms closer to the detector tend to ionize first), and thus the specimen loses atoms from its tip or apex (the area closest to the detector) first, with the tip slowly eroding as evaporation continues. Measurement of the time of flight of the ionized atoms from the specimen to the detector allows determination of the mass/charge ratio of the ions (and thus the identity of the evaporated atoms). Measurement of the location at which the ions impinge on the detector allows determination of the relative locations of the ionized atoms as they existed on the specimen. Thus, over time, one may build a three-dimensional map of the identities and locations of the constituent atoms in a specimen.

Owing to the number of atoms potentially contained in a specimen, and the time required to collect these atoms, specimens are often formed of a sample of a larger object. Such specimens are often formed by removing an elongated core from the object—often referred to as a "microtip"—which represents the structure of the sampled object throughout at least a portion of its depth. Such a microtip specimen is then usually aligned in the specimen holder with its axis extending toward the detector, so that the collected atoms demonstrate the depthwise structure of the sampled object. The rodlike structure of the microtip also beneficially concentrates the electric field of the charged specimen about its apex (its area closest to the detector), thereby enhancing evaporation from the apex.

Ionizing (evaporating) energy need not be delivered solely by means of electric fields. For example, atom probes have been developed wherein the specimen is pulsed thermally, as well as electrically, to assist with evaporation. In some prior arrangements, a laser is situated adjacent to the specimen mount to direct laser pulses at the specimen, thereby briefly heating it to induce evaporation (see, e.g., Kellogg et al., Reference 12 in the accompanying bibliography). However, such arrangements are not common because it can be difficult and time-consuming to focus the laser beam onto a microtip specimen (more particularly, onto its apex). Further, owing to this difficulty, a laser beam of relatively wide diameter is needed, but this undesirably decreases the power density of the laser (unless laser power consumption is increased, which is also undesirable). In addition, the wide beam heats a greater area of the microtip specimen, and such heat can lead to uncertainties in mass determination because the retained heat in the specimen promotes greater variation in ion evaporation times. An alternative approach proposed by Kelly et al. (Reference 1 in the accompanying bibliography) utilizes an electron beam rather than a laser and reduces heating problems, though beam focusing and specimen heating can still pose problems.

As a result, most atom probes enhance evaporation by use of other features. One such feature that may be used is a counter electrode, an electrode with a central aperture, which is situated closely spaced from the specimen between the specimen and detector (see, e.g., Miller at al., Reference 18 in the accompanying bibliography). The counter electrode is usually attractively changed with respect to the specimen so that it will enhance evaporation from the specimen, causing atoms to ionize and fly through the counter electrode's aperture toward the detector. Counter electrodes are generally used for one or more of the following purposes.

First, by situating the aperture of the counter electrode about the apex of the tip, the evaporating electrical field about the apex can be greatly enhanced, thereby allowing the use of evaporating voltage pulses of lower magnitude. Owing to equipment limitations, voltage pulses of lower magnitude usually allow faster pulsing, and thus faster evaporation rates from the specimen (and faster data acquisition). In some cases, counter electrodes are used to concentrate the evaporating field about a selected microtip on a specimen bearing multiple microtips, such that ion evaporation only occurs from the single microtip. In this situation, the counter electrode is often referred to as a "local electrode" since it allows localized evaporation (see, e.g., Kelly at al., Reference 2 in the accompanying bibliography). To achieve more focused evaporation, the local electrode generally has a much smaller aperture than a conventional counter electrode, e.g, on the order of 5-50 micrometers rather than on the order of a few millimeters.

Second, counter electrodes can be used to improve the mass resolution of the atom probe (i.e., to better calibrate measurements of ion times of flight between the specimen and detector). When atom probe voltages are pulsed, atoms tend to evaporate about the peaks of the pulses, leading to a small spread in departure times. Further, a late-departing ion may be in the region of the specimen as the voltage pulse on the specimen decays, and thus the ion may be influenced by the time-varying electrical field emitted by the specimen, leading to greater uncertainty in its true departure time (and thereby in the ion's time of flight, and in the determination of the ion's mass). However, if the counter electrode is situated sufficiently close to the specimen that a departing ion falls under the influence of the counter electrode's electric field before the specimen's voltage pulse significantly decays, the ion's flight will largely be decoupled from the time-varying field, thereby reducing its effect.

Third, counter electrodes are sometimes used to shield the specimen from components in the flight path that might affect the electric fields near the specimen apex. As an example, if an atom probe microscope has a movable detector, the field on the specimen may be increased if the detector is moved closer, thereby enhancing the possibility of ion evaporation at unwanted times and complicating operation. However, the counter electrode, being situated between the specimen and the detector, can partially isolate the specimen from the detector and reduce the influence of the detector's field.

SUMMARY OF THE INVENTION

The invention, which is defined by the claims set forth at the end of this document, is directed to atom probes and methods for their operation which allow advantages over prior atom probes. A basic understanding of some of the preferred features of the invention can be attained from a review of the following brief summary of the invention, with more details being provided elsewhere in this document.

An atom probe includes a specimen mount whereupon a specimen to be analyzed may be mounted, with the specimen mount being chargeable to impart an ionization voltage on a specimen situated within the mount. A detector is spaced from the specimen mount to detect ions evaporated from the specimen. A counter electrode having an electrode aperture is situated between the specimen mount and detector, with the aperture having an aperture entry oriented along an aperture plane. The aperture plane is preferably located at or very close to the specimen apex (i.e., the specimen apex is preferably within, or close to entering, the aperture entry). As in prior atom probes, the specimen mount and detector may be charged to voltages which are nearly sufficient to ionize atoms at the specimen apex, and if desired, "overvoltage" pulses may be applied to the counter electrode to produce timed ionization events wherein ions evaporate when at least some of the pulses are applied. However, ionization is preferably primarily induced by a laser (or other energy beam source, e.g., an electron beam generator) which is spaced from the counter electrode and specimen mount on the opposite side of the aperture plane from the specimen mount, and which is oriented to emit a beam through the aperture of the counter electrode and toward the specimen mount to impinge on the specimen. A laser is a preferred energy beam source because it can be pulsed at very high frequencies, with pulses having widths on the level of picoseconds, thereby generating ionization events at the specimen with far greater mass resolution than in prior atom probes (since ion departures occur over the very narrow window of the laser pulse, allowing ion departure times to be specified with far greater precision).

Where a laser is used, the laser preferably has a beam size substantially smaller than that used in prior laser atom probes such that it has a beam diameter of substantially less than 1 mm upon reaching the specimen. Most preferably, it has a beam diameter of less than or equal to 0.5 mm at the specimen. A smaller beam size (and thus a smaller spot size on the area of interest on the specimen) is useful because it heats less of the specimen, thereby better isolating ionization to the area of interest. Localized heating also promotes more rapid heat dissipation in the specimen, so that retained heat does not promote late ionization and miscalculated ion departure times.

However, situating the laser such that its beam is aligned through the aperture, and using a smaller beam size than in prior atom probes, generates significant difficulties: aligning the beam through the aperture will almost inevitably situate the laser more distantly from the specimen than if the conventional arrangement is used (wherein the laser and specimen are situated on the same side of the counter electrode and its aperture plane, with the laser situated adjacent to the specimen), which makes it difficult to align the beam onto the area of interest on the specimen. This difficulty is compounded as the spot size is decreased, particularly since a smaller beam will be more subject to "drift" (i.e., gradual misalignment over time owing to vibration, laser imperfections, thermal expansion/contraction of the components between the laser and the specimen mount, etc.). Thus, even if a beam can be focused on a specimen apex or other area of interest at the outset of a data acquisition session, data may degrade over time as the beam drifts with usage of the laser.

These difficulties are overcome in two ways. First, coarse alignment of the beam onto the specimen (or at least close to it) is promoted by the use of a counter electrode aperture of small size, preferably of less than about 0.1 mm (and more preferably less than about 0.05 mm). This size is roughly on the order of most microtip atom probe specimens, and since the specimen will be roughly centered in the aperture during atom probe data acquisition form the specimen, one can coarsely align the beam with the specimen by aligning the beam with the aperture. Such alignment can be detected visually, as by monitoring video or microcamera images taken adjacent the specimen mount, and/or by monitoring the output of photodetectors situated about the specimen mount (which can detect laser light projected through the counter electrode aperture).

Fine alignment of the beam may then be attained by use of an automated beam alignment methodology which quickly locates the specimen apex (or other area of interest) without the need for tedious "hunting" by the atom probe's operating personnel. In this methodology, the laser (or other energy beam) is directed toward the specimen and swept in one or more dimensions over a sweep area of predefined size on (or near) the specimen; for example, it might be swept in a sinuous or zig-zagging pattern to cover some sweep area, or it might merely be swept in one dimension along a line. During the sweep, one or more parameters indicative of the interaction between the energy beam and the specimen are monitored. Exemplary parameters of this nature include the collection rate of any ions detected by the detector (with higher collection rates usually tending to be more indicative of the beam's impingement near the specimen apex, where atoms are more likely to ionize); the mass resolution of any ions detected by the detector (i.e., the degree to which detected ions may have their mass/charge ratios clearly correlated to particular atomic species, since good correlation indicates that the ion departure times—which are set by the laser pulse—are being accurately determined); the voltage applied to the specimen mount (since a beam focused on the specimen apex should produce detectable ions at lower specimen voltages than if the beam was not focused on the specimen apex); any reflected portions of the laser beam (since monitoring the image of the reflected beam may show whether the specimen apex is being illuminated); and any scattered portions of the laser beam (since the diffraction pattern of the beam may also indicate whether the specimen apex is being illuminated). The monitored parameters are compared to predefined alignment criteria, for example, whether the parameter(s) for a swept location have acceptable values, and/or whether they indicate that a location along the sweep is more likely near the specimen apex than a prior location.

If a subset of the sweep is found that meets the alignment criteria—for example, if certain swept locations define some subset of the sweep area which have better ionization rates (detector collection rates), ion mass resolution, etc.—a new sweep area can be defined, one which is reduced in size to encompass at least this subset. Most preferably, the parameters are monitored to identify a single location along the sweep which has optimal parameters (those which most closely correspond to a point near the specimen apex), and this location is defined as a "home location" about which the new smaller sweep area is defined. The process is then repeated, with the beam being swept over this new smaller sweep area to locate a new subset of the sweep area (e.g., a single home location) which better meets the predefined alignment criteria, a new reduced sweep area being defined about this subset, and so forth. The process thereby iteratively shrinks and moves the sweep area about the home location, or about the collection of optimal locations, to home in on the specimen apex. Once the alignment criteria are met to some predefined level of accuracy (e.g., once the identified home locations do not significantly change between subsequent sweeps), the sweeping may be halted, and it can be assumed that the specimen apex has been located.

On the other hand, if the parameters monitored during the sweep of the sweep area do not meet the alignment criteria—for example, if they are equivocal regarding the location of the specimen apex—the sweep area is increased rather than decreased before repeating the process, so as to better increase the chances that the areas on the specimen (and more particularly, near its apex) are swept. As an example, a swept area may illustrate little or no change in the monitored parameters from one location to another, indicating that the swept area of the specimen (or perhaps the counter electrode, if the beam has drifted badly) does not seem to be close to the specimen apex at all. The sweep area can then be increased to hopefully locate a home location (or other subarea/subset of the sweep area) that meets the alignment criteria, in which case the process may then iteratively shrink the sweep areas about such locations. Alternatively, if an increased sweep area does not locate a home location or other subarea that meets the alignment criteria, the sweep area can again be increased until a promising subarea is located (at which point the sweep area may be iteratively shrunk about this subarea).

Once the specimen apex (or other desired location on the specimen) has been located by use of the foregoing procedure, atom probe analysis may commence: the specimen, counter electrode, and detector may each be charged to levels conducive to ionization of the specimen, and the laser (or other energy beam source) may be pulsed to add sufficient energy to the specimen that ionization occurs (with the counter electrode being simultaneously pulsed as well, if desired). Since beam drift may occur over time, the foregoing beam fine alignment process may periodically be repeated during data acquisition, perhaps after a certain number of data acquisition cycles occur, and/or after certain parameters (such as evaporation rates, mass resolution, etc.) appear to indicate that the beam is no longer centered on the desired area of the specimen.

The utility of the atom probe is further enhanced if the laser (or other energy beam) contains laser light (or other energy) of at least two different wavelengths when it reaches the specimen. Since different materials can exhibit greater susceptibility to ionization at energies at different wavelengths, using a mixture of wavelengths can enhance the versatility of an atom probe by allowing it to more efficiently analyze a wide range of materials. While a mixture of wavelengths can be generated by using multiple lasers and combining their beams with the use of dichroic mirrors or other elements, a particularly preferred arrangement is to use a single laser (with emitted laser light at a single wavelength), and generate harmonic wavelengths in the same beam by use of nonlinear crystals or other harmonic-generating optics. Using a single laser avoids the need to synchronize pulse timing among different lasers, and also avoids the cost and space issues arising from use of multiple lasers.

Cost and space issues are also reduced if the laser is placed outside of the vacuum chamber containing the specimen mount and detector, and if the laser delivers its beam to the specimen through a window defined in the vacuum chamber (with intermediate mirrors, lenses, or other optical elements being used along the beam if needed). This avoids the need for a laser configured for high-vacuum environments (which can enhance expense), and also avoids the need for the laser to occupy the limited available space within the vacuum chamber. Locating the laser outside the chamber (or at any other location which is distant from the specimen mount) can lead to greater problems with beam alignment on the specimen, but by use of the aforementioned alignment method, these difficulties can be at least partially overcome.

Some of the aforementioned difficulties may also be at least partially alleviated if the aperture of the counter electrode is configured to receive a laser or other energy beam at the entry of the aperture, and concentrate the energy beam before it leaves the exit of the aperture so that the beam is focused on the specimen with greater intensity. This may be done, for example, by configuring the electrode aperture as a concentrating reflector having a parabolic, hyperboloid, or other configuration which internally reflects the beam energy as it travels from a larger aperture entry to a smaller aperture exit so that the incident beam is concentrated to greater intensity when emitted onto the specimen. Such an arrangement can at least partially compensate for beam misalignment by "catching" and redirecting a misaligned beam so that it is focused on the specimen. Since such an arrangement can better tolerate minor beam misalignment, it is also well suited to receive multiple laser or other energy beams and direct any misaligned beams onto the specimen.

Further advantages, features, and objects of the invention will be apparent from the following detailed description of the invention in conjunction with the associated drawings.

BRIEF DESCRIPTION OF THE DRAWINGS

FIG. 2 is an exemplary control and feedback timing diagram for the laser atom probe 100, showing the timing of a control (trigger) pulse PT which triggers a laser pulse PL, thereby generating a timing (pickoff) pulse PP which indicates the timing of the laser pulse PL, and also enabling the detector 106 of FIGS. 1a and 1b so that ion evaporation data may be collected.

FIG. 4 is a process flow diagram illustrating steps of a preferred process used to automatically attain fine alignment of the beam 122 of the laser 116 of FIG. 1a about the apex of the specimen 104.

FIGS. 5a-5c schematically illustrate consecutive iterations of the fine beam alignment process of FHG. 4.

DETAILED DESCRIPTION OF PREFERRED VERSIONS OF THE INVENTION

Figure 1A:
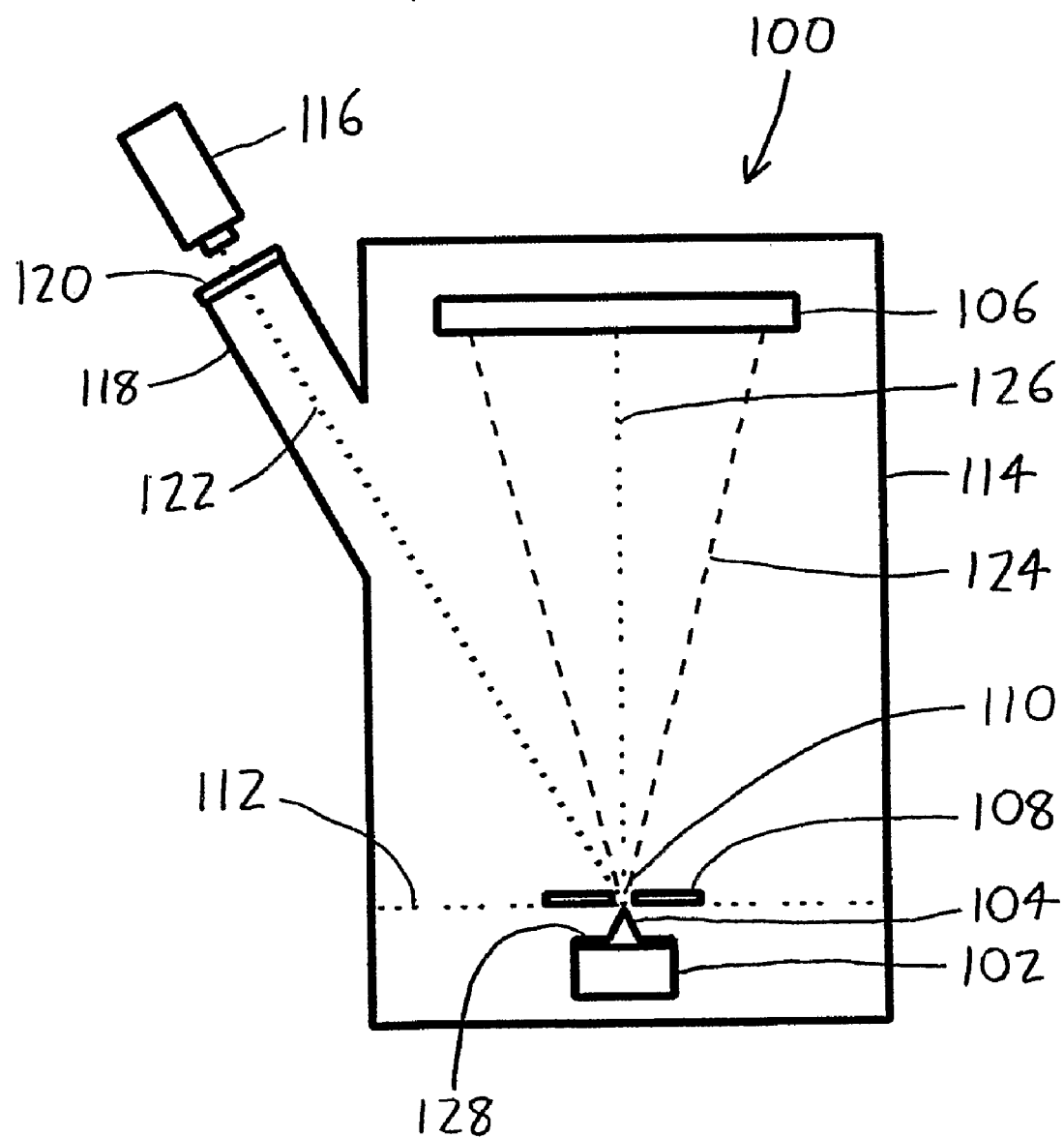
FIG. 1a is a simplified schematic cross-sectional view of a laser atom probe 100, wherein a laser 116 directs its laser beam 122 through the aperture 110 of the counter electrode 108 and onto the apex of the specimen 104.
Figure 1B:
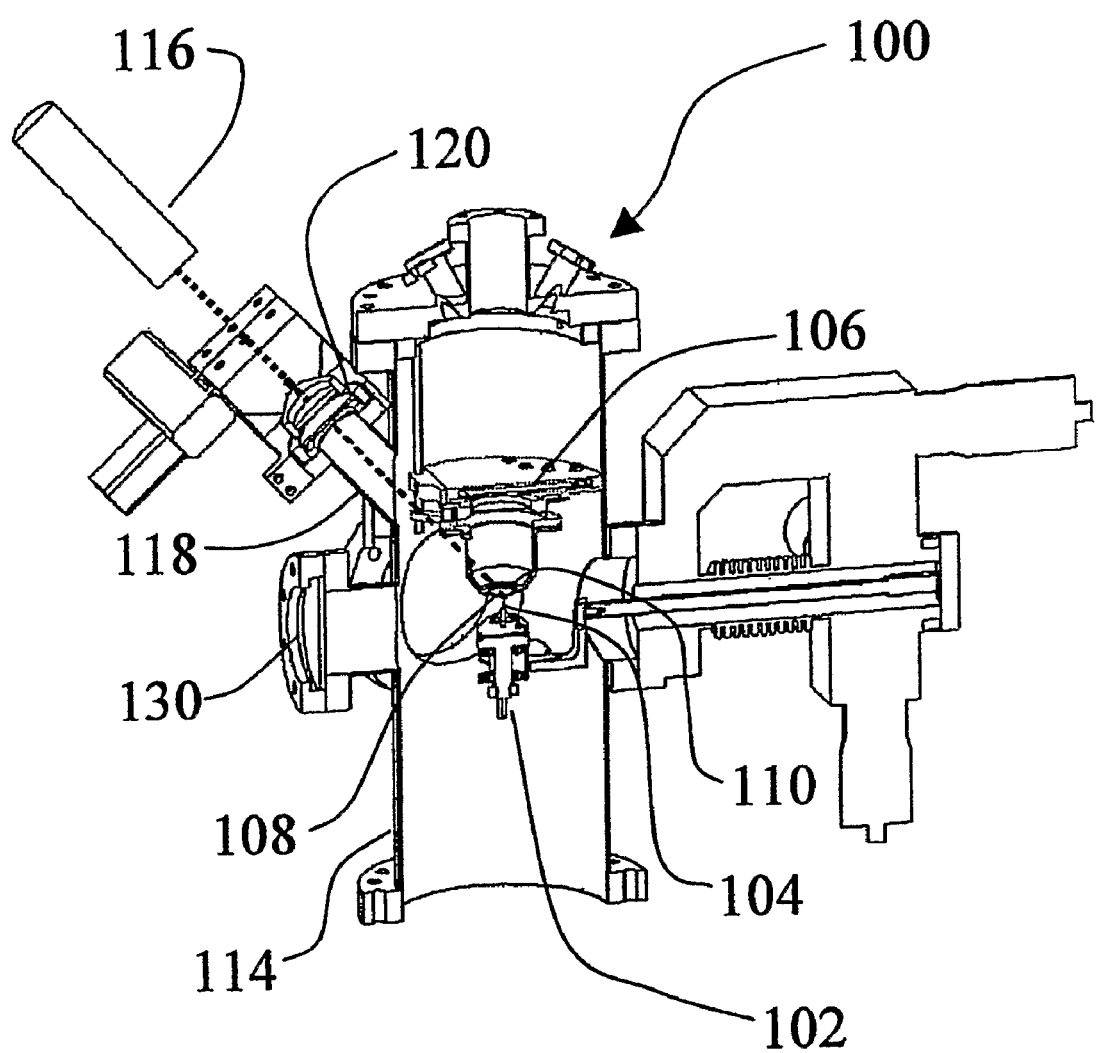
FIG. 1b is a perspective cross-sectional view of a prototype laser atom probe corresponding to the laser atom probe 100 of FIG. 1.

Turning initially to FIGS. 1a and 1b, an exemplary laser atom probe, depicted generally by the reference numeral 100, is illustrated in both schematic form (FIG. 1a) and in a perspective view of an actual prototype (FIG. 1b). The laser atom probe 100 includes a specimen mount 102 with a specimen 104 mounted thereon, an opposing detector 106 for receiving ions evaporated from the specimen 104, and a counter electrode 108 situated between the specimen mount 102 and the detector 106. The specimen mount 102 is movable to allow positioning of the specimen 104 within or closely spaced from the aperture 110 of the counter electrode 108, with the apex or other area of interest on the specimen 104 preferably being situated at the aperture plane 112 which defines the entry of the aperture 110. A vacuum chamber 114 surrounds all of the foregoing components. As can be seen from the references noted in the Bibliography provided later in this document, the foregoing arrangement of the specimen mount 102, detector 106, and counter electrode 108 are conventional in the field of atom probes, though a variety of configurations and operating modes are possible. As examples, the counter electrode 108 may take the form of a local electrode (as shown in U.S. Pat. No. 5,440,124, Reference 2 in the Bibliography); additional counter or "intermediate" electrodes may be present (as shown in U.S. Pat. No. 6,580,069 to Cerezo, Reference 4 in the Bibliography); or other features may be present. In one conventional mode of operation, the specimen mount 102 and detector 106 are charged to "boost" voltages which are nearly sufficient to cause ionization of the specimen 104 (generally with the specimen mount 102 being charged to about 75% of the ionization energy threshold), usually with the specimen 104 being positively charged and the detector 106 being negatively charged. The counter electrode 108 and/or the specimen mount 102 may then be pulsed with an "overvoltage," i.e., with a charge surpassing the ionization threshold of the specimen 104, so that ions are evaporated during the pulses (and their flight times to the detector 106 can be measured from the pulses).

The foregoing arrangement may be adapted to adjust the conventional atom probe for use as the laser atom probe 100 by providing a laser 116 which is oriented to project its beam through the aperture 110 of the counter electrode 108, and onto the apex or other area of interest on the specimen 104. In the exemplary laser atom probe 100 of FIGS. 1a and 1b, the vacuum chamber 114 includes a viewing tube 118 ending in a window 120, and the laser 116 is situated outside the window 120 to emit its beam 122 through the window 120 and subsequently through the counter electrode aperture 110. However, as discussed later in this document, other placements for the laser 116 are possible as well (e.g., within the chamber 114).

Several operational modes are possible, with two being particularly preferred. In one mode, the specimen mount 102 may be charged to some boost voltage amounting to a significant fraction of the ionization energy threshold, and the remainder of the ionization energy may be provided by the laser 116, which is pulsed to deliver ionization energy to the specimen 104 in much the same manner as conventional overvoltage pulses. In this case, the counter electrode 108 may simply serve as an uncharged ground plane.

In a second mode, the boost voltage is again applied by the specimen mount 102, and the remaining ionization energy may be shared by the laser 116 and counter electrode 108. In this case, the counter electrode 108 provides overvoltage pulses which bring the specimen 104 close to ionization, and the laser 116 then provides the energy necessary to cause ion evaporation. With this arrangement, the boost voltage can be decreased, and thus stress on the specimen 104 may be decreased, since the combined energy imparted by the laser 116 and counter electrode 108 may constitute a greater amount of the total energy needed to surpass the ionization threshold.

To describe the prototypical laser atom probe 100 of FIG. 1b in greater detail, it uses an atom probe manufactured by Imago Scientific Instruments Corporation (Madison, Wis. USA) with a laser 116 having a diode-pumped Ti:Sapphire oscillator (the Verdi-V5 pump laser with a Mira Optima 900-F cavity, both from Coherent, Inc., Santa Clara, Calif., USA), which produces 8 nJ pulses at a nominal repetition rate of 76 MHz. A cavity dumper (the Pulse Switch cavity dumper from Coherent, Inc.) is used to increase the pulse energy to 60 nJ and decrease the repetition rate to 100 KHz. These components are merely exemplary, and other suitable equipment allowing the same or different outputs is available from Coherent, Inc. or from other laser equipment suppliers such as Spectra-Physics, Inc. (Mountain View, Calif., USA). The aforementioned Coherent, Inc. Pulse Switch cavity dumper includes second and third harmonic generators, which may be beneficially utilized in a manner to be discussed later in this document.

The pulsed beam 122 of the laser 116 is then directed through the window 120 and the counter electrode aperture 110, and onto the apex or other area of interest on the specimen 104. The laser beam 122 is oriented at an angle of slightly less than 45 degrees relative to the ion travel axis (i.e., the center of the cone defined by the flight paths of the ions from the specimen 104, with the flight cone being designated in FIG. 1a at 124 and the ion travel axis being designated at 126). This angle is suitable to prevent the beam 122 from intersecting with the flight cone 124, while at the same time allowing the beam 122 to impinge on the specimen 104 through the counter electrode aperture 110. However, if the components of the atom probe 100 are altered (e.g., if the size of the counter electrode aperture 110 and/or the length of flight path 126 are changed), the angle of the beam 122 may vary.

In the prototypical atom probe 100, the flight path 126 is nominally 6 cm (though this may be adjusted, most easily by moving the detector 106). Such a flight path 126 beneficially allows data acquisition cycles on the order of 1 MHz, thereby greatly reducing the time for specimen analysis (on the order of minutes instead of hours or days), thereby greatly enhancing the industrial applicability of the atom probe 100. Longer (or shorter) flight paths may be used with corresponding impact on data acquisition rates: as the flight path grows longer and/or as the pulse frequency grows more rapid, the start of one data collection cycle will begin overlapping with the end of the prior data collection cycle, leading to greater data interpretation and control burdens. Adjustment of the flight path 126 will also have corresponding effects on field of view and magnification (with magnification being proportional to flight path length and field of view being inversely proportional), with the 6 cm flight path providing a field of view between 1.5-2.0 steradians.

The counter electrode 108 may take planar, concave, or other forms, with the prototypical laser atom probe 100 using a planar counter electrode having an aperture 110 which preferably has a diameter of less than about 0.05 mm. Larger apertures 110 are possible, though it is preferred that they have diameters of less than 0.1 mm; as will be discussed later in this document, the use of a smaller aperture greatly assists with the nontrivial task of focusing the laser 116 (which is far more distant than in prior laser atom probes) onto the specimen 104. Further, a conical or other concave counter electrode 108 having an aperture 110 of the same order or smaller might be useful if the counter electrode 108 is to serve as a local electrode, e.g., for analysis of individual adjacent microtips on the same specimen 104.

The laser 116 uses a more tightly focused beam 122 than in prior laser atom probes, preferably of less than 1 mm diameter and more preferably less than 0.5 mm (as received at the specimen 104). The prototypical atom probe 100 has a spot size (beam diameter) of approximately 0.02 mm at the specimen 104. This beneficially reduces the volume of the specimen 104 that is subjected to laser heating, resulting in better heat dissipation and thus reducing the time-of-departure spread for ionized atoms (i.e., less energy is retained in the specimen 104, thereby deterring later ionization events after the pulse is delivered). Additionally, since a lower-diameter beam 122 has greater power density than a larger-diameter beam (assuming the same input power), use of a lower-diameter beam 122 allows the use of lower power (and less expensive) lasers 116. For example, if one compares two beams of equal power density, one having a diameter of 0.05 mm and the other having a diameter of 1 mm, the 0.05 mm beam only needs 1/400 the power of the 1 mm beam (since power density varies in accordance with the square of the diameter).

A variety of collimators, lenses, and other optics may be used to focus the beam 122, and the focusing optics will be dependent on the laser 116 chosen for use in the atom probe 100. The prototypical atom probe 100 of FIG. 1b utilizes a coated biconvex lens (model PLCX-38.1-103.0-UV-355-532, CVI Laser LLC, Albuquerque, N.Mex., USA) mounted on a conventional positioning stage (Model 423) fitted with motorized actuators (Model LTA-HS), both provided by Newport Corp., Irvine, Calif., USA. These components, which are not shown in the drawings, are situated outside of the vacuum chamber 114 adjacent the viewport 120. The positioning stage therefore allows repositioning of the focusing lens to attain the desired beam diameter/spot size at the specimen 104.

FIG. 2 provides a plot of control and feedback signals over a single data acquisition cycle. The control system for the laser atom probe 100 (a personal computer) delivers a trigger pulse PT to the laser 116. After receiving the trigger pulse PT, the cavity dumper of the laser 116 releases the next available laser pulse PL. Since an indeterminate amount of time Ti passes between the trigger pulse PT and the generation of a laser pulse PL, a fast photodiode is used to generate a pickoff pulse PP which may then be used by the control system as the nominal pulse departure time Tp (and in turn as the departure time of any ion subsequently detected at the detector 106). Rather than constantly (and unnecessarily) collecting data from the detector 106, data acquisition at the detector 106 is enabled after the passage of a small period of time T2 after the pickoff pulse PP (at Td), thereby better limiting data collection to ion arrivals. The mass-to-charge ratio of the detected ions (and thus the identities of their atoms) can then be determined by subtracting Tp from the arrival time. Data acquisition at the detector 106 is disabled at some fixed period of time (typically 1 microsecond) after Td, and before the next data acquisition cycle begins. The timing of pulses on the counter electrode 108 is not depicted because FIG. 2 assumes that the counter electrode 108 merely acts as an uncharged ground plane. However, if the counter electrode 108 was to be charged, a counter electrode pulse of the desired magnitude could be initiated by the trigger pulse PT, and could have sufficient pulse width that the laser pulse PL will occur over its duration. In this manner, the counter electrode pulse would serve as an overvoltage pulse which steps the specimen 104 to a level near its ionization energy, and the laser pulse PL would then supply the energy sufficient for ionization.

For efficient ionization, it is useful to accurately know the beam diameter and power density of the laser beam 122 (and thus the amount of ionization energy being delivered by the beam 122). This can be done in a variety of ways. Most preferably, measurements are taken at or shortly after the aperture plane 112 such that the energy input at the apex of the specimen 104 can be inferred. A first way to accomplish this is to situate photosensors adjacent to the specimen mount 102 in FIG. 1a (or on or in place of the specimen mount 102 before it is fully moved into place), and directly measure the output of the beam 122. An exemplary arrangement of this nature is depicted in FIG. 1a, wherein a photosensor array 128 is situated about the edges of the specimen mount 102. Measurements at the aperture plane 112 can be calculated from the measurements taken from the location of the photosensors 128. Another approach is to use mirrors near the specimen mount 102 in FIG. 1a (or in place of the specimen mount 102 before the specimen mount 102 is moved into place), with the mirrors delivering the reflected beam 122 to a photosensor within or outside the vacuum chamber 114 (e.g., through a viewport in the vacuum chamber 114) to allow calculation of the beam power at the aperture plane 112. Other approaches include building a photosensor into the counter electrode 108, or temporarily moving a photosensor immediately above or below the counter electrode 108 (as with the foregoing approach of placing the photosensor 128 on the specimen mount 102), to more directly measure the beam 122 at the aperture plane 112. Other approaches using photosensors inside or outside the chamber 114, and with or without any mirrors or other optical elements between the laser 116 and photosensor, are also possible.

As previously noted, the laser 116 is used with second and third harmonic generators, thereby allowing tuning of the mean wavelength of the beam 122 from the ultraviolet to the near-infrared ranges and allowing the wavelength to be adjusted to better induce ionization in specimens 104 of different materials. However, in some cases, a single wavelength does not result in efficient ionization owing to material differences in the specimen 104, with the single wavelength failing to efficiently couple with all components present in the specimen 104. The prototypical atom probe 100 therefore preferably uses a beam 122 containing multiple wavelengths. While this could be done by using multiple lasers 116 directing their beams 122 onto the specimen 104, perhaps after combining their beams 122 with the use of dichroic mirrors or other elements, the use of multiple separate lasers 116 leads to added space and expense, and also leads to added complexity, particularly regarding the need to synchronize pulse timing among different lasers. Therefore, a particularly preferred arrangement is to use the single laser 116 and generate harmonic wavelengths in the same beam 122 by interposing nonlinear crystals or other harmonic-generating optics in the path of the beam 122. In the prototypical atom probe 100 of FIG. 1b, the beam from the laser 116 is focused into a nonlinear crystal (such as a BBO crystal from EKSMA Photonics Components, Vilnius, Lithuania), which is not depicted in the accompanying drawings. The crystal allows production of a second harmonic wavelength in the beam 122 (having half of the wavelength emitted by the laser 116) with approximately 50% conversion efficiency. If desired, subsequent nonlinear crystals may be placed in the path of the beam 122 to produce a third harmonic (having one-quarter of the wavelength emitted by the laser 116), a fourth harmonic, and so forth. Achromatic lenses/collimators and/or other optical components may be used to focus and adjust beam diameters for each wavelength so that when they enter the counter electrode aperture 110 and impinge upon the specimen 104, they will all be focused to the same beam diameter.

To summarize, use of the laser 116 provides significant operational advantages over conventional atom probes. One primary advantage is that conventional atom probes are generally limited to analysis of specimens 104 which are at least substantially conductive, since nonconductive specimens 104 require significantly higher boost voltages and overvoltages (and the electric fields of these higher voltages cause substantial stress on the specimen 104, which may then mechanically fracture). Since the laser 116 allows operation at significantly lower voltages, the laser atom probe 100 allows analysis of even significantly nonconductive specimens 104, such as organic specimens 104. As a related advantage, the wavelength(s) of the laser 116 (or lasers) used to generate the beam 122 may be adapted for more efficient ionization of specimens 104 of different types, including those which have nonheterogeneous compositions (e.g., specimens 104 containing both conductive and nonconductive regions, inorganic and organic regions, etc.).

Another primary advantage is that a suitable laser 116 can generate pulses having widths on the order of picoseconds or femtoseconds. Since specimen ionization occurs over the very narrow window of the laser pulse, ion departure time may be specified with far greater precision, thereby allowing far greater mass resolution than in conventional atom probes (better than 1 in 500 mass-to-charge units). Further, the pulses can be generated with frequencies of 1 kHz-1MHz, thereby allowing extremely rapid data collection.

However, despite these advantages, the foregoing arrangement introduces several significant challenges, in particular difficulties with accurate focusing of the beam 122 on the specimen 104. Since the laser 116 is situated distantly from the specimen 104, and has a preferred spot size of less than 0.5 mm (with the prototypical atom probe 100 having a spot size of 0.02 mm), focusing the beam 122 onto the apex of the specimen 104 —which may itself have a diameter on the order of tenths or hundredths of millimeters —is not trivial, particularly since the beam 122 may drift over time owing to environmental vibration, thermal expansion and contraction of atom probe components, and so forth. Prior laser atom probes (such as that in References 20 and 21 of the accompanying Bibliography) reduced these difficulties by closely situating the laser 116 adjacent the specimen 104 and on the same side of the aperture plane 112, and using a far larger spot/beam diameter, thereby making it easier to direct the beam onto the apex or other area of interest on the specimen. Even then, the process of focusing the beam onto the desired area of the specimen, and keeping it properly aligned, was not a trivial matter; focusing required methods such as visual inspection of fluorescence or field ion microscopy, which are subject to interpretation. These approaches are also time-consuming in that they require that some small amount of gas be introduced into the vacuum chamber, and then pumped out again before atom probing can be initiated. When it is then considered that reducing the beam diameter, and situating the laser more distantly from the specimen, will both make initial focusing more difficult and will also require periodic checking for drift during an atom probe data acquisition session, it would seem that the foregoing arrangement for the atom probe 100 would not be worthwhile—particularly since drift checking would require interruption of data acquisition for time-consuming consuming introduction and removal of gas into the vacuum chamber 114, which would be intolerably tedious.

However, many of these disadvantages can be avoided by use of the following beam alignment methodology, which first involves a coarse beam alignment, followed by specimen alignment, and finally a fine beam alignment. The coarse beam alignment may be performed only once upon the first installation and use of the atom probe 100, and only infrequently thereafter between data acquisition sessions. Specimen alignment is then performed prior to each data acquisition session. Fine beam alignment is then preferably performed both prior to and during data acquisition sessions to protect against beam drift.

Coarse beam alignment is performed by focusing the beam 122 through the aperture 110 of the counter electrode 108. A preferred method of coarse alignment is as follows:

1. Power on the laser 116 and wait for the position of the beam 122 to stabilize (usually 15 minutes or so is sufficient).
2. Activate the photosensor (e.g., the photosensor array 128 depicted in FIG. 1a). As previously noted, the photosensor is preferably positioned (at least temporarily) generally along the ion travel axis 126 on the specimen side of the aperture plane 112, or may otherwise be situated on the counter electrode 108 or at other locations (including locations outside the vacuum chamber 114) which allow determination of whether the beam 122 is passing through the electrode aperture 110. Again, a particularly preferred arrangement is to have a movable photosensor 128 which moves immediately adjacent the counter electrode 108 on the specimen side of the aperture plane 112, so that the photosensor 128 can be situated at generally the same location at which the apex of the specimen 104 will rest during later data acquisition.
3. Starting with a defocused beam 122, obtain an initial signal on the photosensor 128 by translating the beam using beam steerers (i.e., mirrors, collimators, and the like, which are not depicted in the drawings). Such beam steerers are preferably located outside the viewport 120, though they could instead be located within the vacuum chamber 114.
4. Translate the beam 122 until the signal on the photosensor 128 is maximized, thereby indicating that the entire unfocused beam 122 is passing through the aperture 110 without impinging on the counter electrode 108 at the borders of the aperture 110.
5. Focus the beam 122 to maximize the signal on the photosensor 128.
6. Repeat the foregoing steps 4 and 5 iteratively until the maximum signal is obtained on the photosensor 128.
7. Adjust the power of the beam 122 to the desired level.

Coarse beam alignment is then complete, and the settings for the beam steerers, focusing optics, laser power controls, etc. may be secured. The coarse alignment procedure may be performed upon initial startup and installation of the atom probe 100, and is also beneficially performed after maintenance or refitting of the atom probe 100, e.g., if a new counter electrode 108 is installed, or if additional counter electrodes (often referred to as intermediate electrodes) are installed between the counter electrode 108 and the detector 106. Otherwise, the coarse alignment procedure may not need to be repeated after initial startup. However, keeping in mind that preferred versions of the atom probe 100 have apertures 110 of less than 0.1 mm (and preferably on the order of 0.05 mm), it is useful to perform periodic coarse alignment checks after every few data acquisition sessions to verify that gross drift has not misaligned the beam 122 from the aperture 110. If the atom probe is used with counter electrodes 108 having larger apertures 110 (e.g., on the order of 2.5 mm or more, which is more conventional), the need to repeat coarse alignment is not as critical.

Other coarse alignment methods are also possible, with use of the photosensor 128 merely being a preferred method. Coarse alignment could instead be performed, for example, by using a long-range microscope and a videocamera. It is also possible to combine photosensors and imaging devices in the coarse alignment process.

Note that in essence, the counter electrode aperture 110 serves as the focal point for alignment of the beam 122 with the apex or other area of interest on the specimen 104: aligning the (movable) beam 122 with the (movable) specimen 104 can be challenging and time-consuming, but by using the counter electrode 108—which is at a fixed location within the vacuum chamber 114 of the atom probe 100—as the focal point for the beam 122 (since the specimen 104 will be centered in its aperture 110 during data acquisition), the alignment process is greatly simplified. Further note that when the atom probe 100 is later operated in such a mode that the counter electrode 108 is an uncharged ground plane during data acquisition, alignment of the beam 122 is effectively the primary purpose of the counter electrode 108: if beam alignment was not a concern, the counter electrode 108 could be eliminated.

After coarse beam alignment is complete, alignment of the specimen 104 with the counter electrode aperture 110 may be performed in a variety of ways. One preferred method of specimen alignment is to initially use two orthogonal optical microscopes for coarse specimen alignment, and if necessary, follow coarse specimen alignment with field ion microscopy for fine specimen alignment. The coarse specimen alignment process is as follows:

1. Ensure that the laser 116 is off, or that its beam 122 is shuttered.
2. Move the specimen mount 102 until the specimen 104 is roughly aligned with the counter electrode aperture 110.
3. Using 2-axis translation of the specimen 104 (along the plane perpendicular to the ion travel axis 126), move the specimen mount 102 such that the specimen 104 is situated generally along the ion travel axis 126. Optical microscopes orthogonally situated about the ion travel axis 126 at the general location of the aperture plane 112 can be used to verify alignment along both axes of translation. (Such microscopes are not shown in the drawings, but can be usefully provided outside the vacuum chamber 114 to view the specimen at appropriately-located viewports, one such viewport being shown in FIG. 1b at 130.)
4. The specimen mount 102 can then be moved parallel to the ion travel axis 126 until the apex or other area of interest on the specimen 104 is situated generally on the aperture plane 112 (i.e., so that the apex of the specimen 104 is situated just outside or within the counter electrode aperture 110).

If necessary, fine specimen alignment can be accomplished using field ion microscopy (FIM):

1. An imaging gas (e.g., neon) is introduced into the vacuum chamber 114 of the atom probe 100. An imaging gas pressure of approximately $5 \times 10^{31.6}$ mbar is usually sufficient.
2. The gain of the detector 106 is adjusted to an appropriate level for FIM.
3. Voltage is then supplied to the specimen mount 102 (and thus the specimen 104) until an image of the apex of the specimen 104 can be obtained on the detector 106.
4. The specimen 104 is translated along the two axes of the aperture plane 112 until an unobstructed image is obtained on the detector 106. If the specimen 104 is misaligned, the counter electrode 108 will occlude a portion of the image.

Fine beam alignment is then preferably performed after specimen alignment, and also periodically during the course of data acquisition to ensure that the beam 122 is still aligned with the apex or other area of interest on the specimen 104. Fine alignment could be performed using FIM methods such as those described by Kellogg et al. and Cerezo et al. (References 10 and 12 in the Bibliography at the end of this document). In these methods, the FIM is driven by both the laser 116 and by the voltage applied to the specimen 104, and the specimen position is constantly adjusted while at the same time adjusting beam power and specimen voltage to obtain an appropriate image. However, since the atom probe 100 preferably uses beam 122 diameters of less than 1 mm, and more preferably less than 0.5 mm (with the prototypical atom probe 100 of FIG. 1b using a preferred beam diameter of approximately 0.02 mm), it is found that prior alignment schemes are exceedingly difficult and tedious because they are extremely sensitive to beam alignment: with a narrow beam, very small changes in beam position require very large corrections in beam power and/or specimen voltage. This is because the sensitivity of the FIM is roughly approximate to the inverse of the beam diameter. As a result, significant time may be needed to accurately align a small-diameter beam to a specimen 104.

Further, when it is considered that FIM sensitivity varies with the inverse of the beam diameter, it should be apparent that the atom probe 100 is extremely sensitive to beam drift (which can readily misalign a small-diameter beam 122 from the apex of the specimen 104). Thus, data acquisition may be drastically impeded by beam drift occurring during a data acquisition session. If large-diameter beams of greater than 1 mm are used (as in prior laser atom probes), drift is not a significant problem since the large-diameter beam can still impinge on the apex of the specimen 104 even if drift occurs. However, as the beam diameter is decreased below 0.5 mm—which begins to approach the range of drift that can occur from standard environmental factors (such as vibration, thermal expansion/contraction, etc.)—drift becomes a key concern, particularly as the beam diameter is decreased to the range of hundredths of millimeters (or smaller). Since it would be plainly impractical to halt a data acquisition session to introduce imaging gas, perform FIM, and then re-evacuate the vacuum chamber 114 to resume data acquisition, the utility of the atom probe 100 is greatly enhanced if improved methods of fine beam alignment are used.

Figure 3:
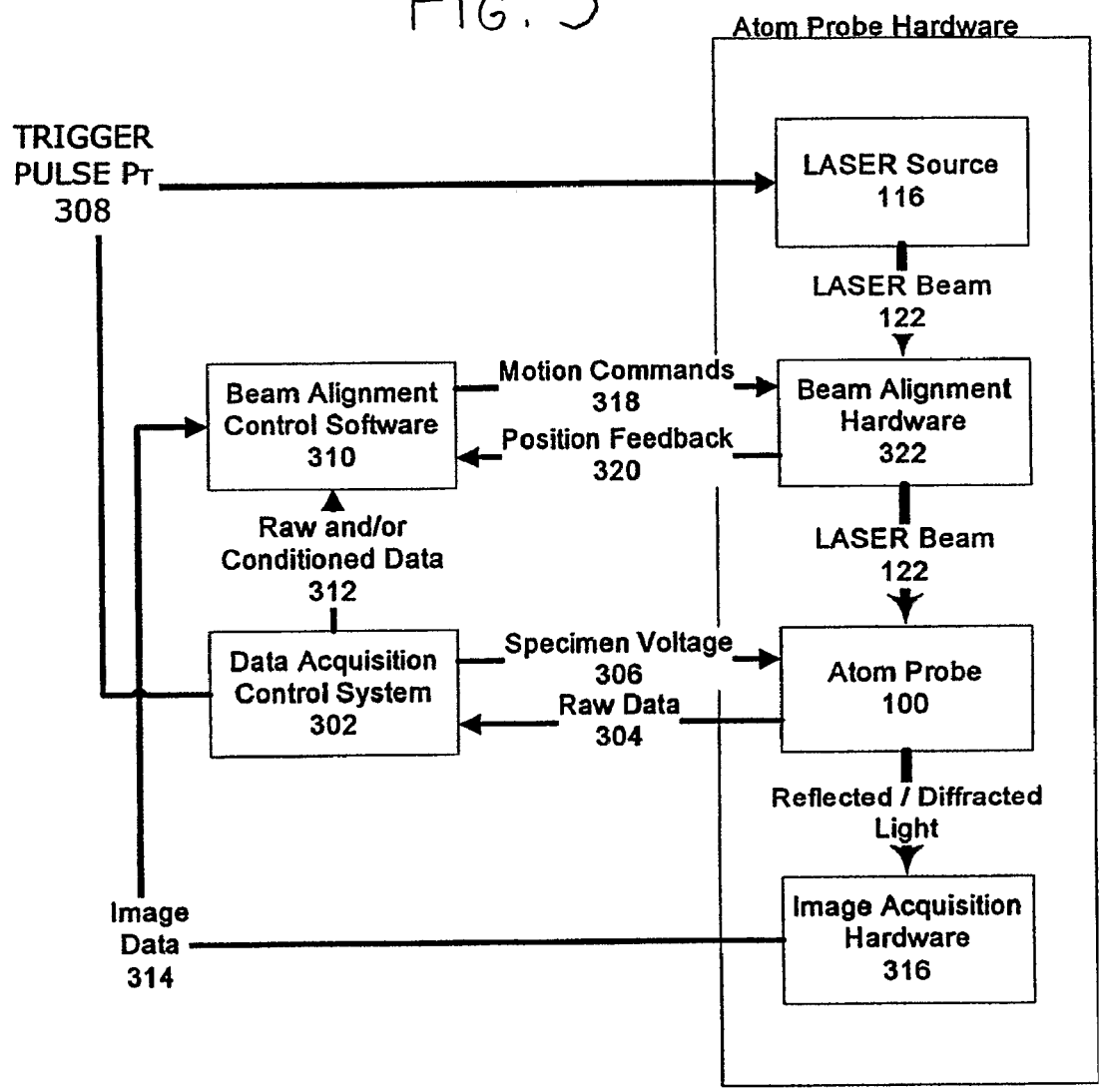
FIG. 3 is a schematic diagram of an exemplary control system for attaining fine alignment of the beam 122 of the laser 116 of FIG. 1a about the apex of the specimen 104.

An exemplary control system for fine beam alignment is then shown in FIG. 3, and is designated generally by the reference numeral 300. A data acquisition control system 302 receives raw data 304 from the atom probe 100, and adjusts the (DC) specimen voltage 306 applied to the specimen mount 102 (and in turn to the specimen 104) in accordance with the data 304. This data acquisition control loop repeats throughout the fine beam alignment process and continually adjusts the specimen voltage 306 to obtain a controlled rate of field ionization. The data acquisition control system 302 also supplies the trigger pulse 308 (also shown as PT in FIG. 2) to the laser 116, and encodes the departure time of the resulting laser beam pulse (via the pulse pickoff signal PP in FIG. 2). A second control loop, which runs synchronously or asynchronously with respect to the control loop of the data acquisition control system 302, is executed by a beam alignment control system 310. The beam alignment control system 310 receives raw and/or conditioned atom probe data 312 from the data acquisition control system 302, and also receives image data 314 from image acquisition hardware 316 (videocameras or other optical imaging devices which monitor the specimen 104 within the vacuum chamber 114), and in turn provides motion commands 318 to (and receives position feedback 320 from) beam alignment hardware 322. The beam alignment hardware 322, which is not illustrated in FIGS. 1a or 1b, may be provided by one or more actuators for adjusting the direction of the laser beam 122, and may take the form of actuators which adjust the position of the laser 116 and/or mirrors, lenses, or other optics along the path of the laser beam 122.

Within the beam alignment control system 310, the atom probe data 312 and image data 314 are conditioned to generate one or more control parameters which are indicative of the interaction between the laser beam 122 and the specimen 104, and which are used by the beam alignment control system 310 to finely (and automatically) adjust the alignment of the laser beam 122:

(1) Evaporation rate (the collection rate of any ions detected by the detector 106): The evaporation rate of the specimen should increase as the laser beam 122 approaches the apex of the specimen 104, since the field strength is also strongest at this area of the specimen 104, and therefore the laser beam 122 should induce ionization more easily at the apex than elsewhere on the specimen 104. Accordingly, if the beam alignment control system 310 seeks the area on the specimen 104 with the maximum evaporation rate, there is a high likelihood that this area will correspond to the specimen apex.

(2) The voltage applied to the specimen 104. In similar fashion, as the laser beam 122 approaches the apex of the specimen 104, it should be able to induce evaporation with a lower specimen voltage. Thus, if the beam alignment control system 310 seeks the area on the specimen 104 where evaporation can be maintained with minimum voltage on the specimen 104, there is a high likelihood that this area will correspond to the specimen apex.

(3) Mass resolution of detected ions. An ion's arrival time can be determined from the detector 106, and if the ion departure time is well known, the mass/charge ratio of the ion should correlate well with known values to allow identification of the ion. However, as the departure time grows uncertain, the correlation decreases. In the laser atom probe 100, departure time variations will begin to increase if it takes longer for the heat of the laser beam 122 to dissipate (i.e., as the effective width of the laser pulse grows wider). Since sensitivity to heat dissipation should be greatest at the apex of the specimen, if the beam alignment control system 310 adjusts the alignment of the laser beam 122 to find the area on the specimen 104 with the lowest uncertainty in mass resolution, there is a high likelihood that this area will correspond to the specimen apex.

(4) Signal-to-noise ratio. Similar to mass resolution (item (3) above), the signal-to-noise ratio of the atom probe data is limited by the quality of the beam alignment: as the laser beam 122 deviates from the apex of the specimen 104, well-timed evaporation will decrease and unplanned evaporation will increase. The signal and noise floors will therefore approach each other as the beam 122 deviates from the apex of the specimen 104, and will diverge as the beam approaches the apex. Thus, if the beam alignment control system 310 adjusts the alignment of the laser beam 122 to find the area on the specimen 104 with the highest signal-to-noise ratio, there is a high likelihood that this area will correspond to the specimen apex.

(5) Reflected light from the specimen. The image acquisition hardware 316 (i.e., videocameras or other optical imaging devices which monitor the specimen 104 within the vacuum chamber 114) can monitor the specimen 104. The apex of the specimen 104 will have a greater tendency to reflect and/or fluoresce when illuminated by the laser beam 122. Therefore, the beam alignment control system 310 can adjust the alignment of the laser beam 122 to find the area on the specimen 104 with peak intensity (or other reflection/emission characteristics), and thereby have a higher likelihood of illuminating the apex of the specimen 104.

(6) Diffracted light from the specimen. Diffracted light is more usefully monitored to maintain alignment of a beam than to initially align a beam 122. Here, the far-field (Fraunhofer) diffraction pattern produced by the specimen 104 can be monitored by the image acquisition hardware 316, and the beam alignment control system 310 can adjust the alignment of the laser beam 122 to maintain a constant diffraction pattern, thereby helping to ensure that the beam 122 maintains alignment with the apex of the specimen 104 once focused on this location.

There are other possible control parameters which are indicative of the interaction between the laser beam 122 and the specimen 104, and which can be used to instruct the beam alignment control system 310 to make alignment corrections. It is also possible (and advisable) to have the beam alignment control system 310 use more than one of these variables, with appropriate weights applied to each selected variable, to better allow the beam alignment control system 310 to more rapidly locate the apex of the specimen 104.

A preferred fine alignment process for the laser beam 122 then proceeds in the manner illustrated in FIG. 4. Initially, at step 402, the user verifies to the beam alignment control system 310 that coarse alignment has been performed, thereby providing reasonable assurance that the beam 122 is directed through the counter electrode aperture 110 onto the specimen 104 (or its immediate area).

At step 404 in FIG. 4, the user then specifies (or the beam alignment control system 310 defines or recalls) a sweep path—a beam path in the plane perpendicular to the ion travel axis 126—about which the beam 122 will be swept. The beam alignment control system 310 will simultaneously monitor one or more of the aforementioned control parameters (see step 406 in FIG. 4) to seek to meet some predefined alignment criterion, i.e., a standard which is characteristic of the apex of the specimen 104. For example, the beam alignment control system 310 might verify whether the parameter(s) for a swept location has values within a range that would be expected for beam impingement on the apex of the specimen 104; whether the parameter(s) indicates that a location along the sweep is more likely near the apex of the specimen 104 than a prior location; and/or whether the parameter(s) "optimally" indicates the apex of the specimen 104 (e.g., whether a location along the sweep has the highest evaporation rate, which would seem to indicate the apex of the specimen 104). In essence, the objective is to identify the location(s) along the sweep which optimizes the control parameter(s), thereby locating some point(s) or segment along the sweep path which is believed to be closer to the apex of the specimen 104.

The sweep area can assume a wide variety of sizes and shapes, with an initial sweep area preferably having a size on the order of the diameter of the counter electrode aperture 110. As examples, the sweep area might be a circular or square area which can be swept in a spiraling, sinuous, or zig-zagging pattern so that much of the sweep area (and thus some portion of the specimen 104) is swept. Alternatively, as will be discussed below, the sweep area might be defined as a narrow lane, and the sweep might simply occur in one dimension to sweep along the sweep area in a straight line.

While performing the initial sweep of the sweep area, the beam alignment control system 310 will identify the point or other subset of the sweep which has control parameters which meet the alignment criteria (i.e., which appear to be more promising candidate locations for the apex of the specimen 104). After completion of the initial sweep, the beam alignment control system 310 will then take one of two paths to redefine the initial sweep area (step 408 in FIG. 4):

(1) If the beam alignment control system 310 did identify some subset of the sweep having control parameters which best met the alignment criteria—i.e., some single location (a "home location") was located with control parameters that were optimal in comparison to all locations swept along the sweep area, or if some collection of points most closely met the alignment criteria (e.g., the 10% of sampled locations having the most promising control parameters)—the beam alignment control system 310 will automatically define a new sweep area, one which is reduced in size to encompass at least this subset. As an example, if a single optimal home location is identified, a new sweep area might be defined which is 50% the size of the initial sweep area, and which is preferably centered about the home location.

(2) If the beam alignment control system 310 did not identify some subset of the sweep having control parameters which met the alignment criteria—for example, if all sampled locations along the sweep area had control parameters which did not deviate from each other by more than 10%—the sweep area can be increased rather than decreased (for example, its borders might be expanded outwardly by 50%), since such a result would appear to indicate that the apex of the specimen 104 is not within the sweep area. Alternative approaches are possible; for example, the beam alignment control system 310 could simply define another initial sweep area having the same size, and which is offset from the first in some direction in the plane perpendicular to the ion travel axis 126. If this sweep area does not result in at least one location having control parameters which met the alignment criteria, the beam alignment control system 310 can continue to define sweep areas about the initial one until some promising location(s) is found.

Once the sweep area is redefined in step 408, the process may continue to step 410, and a new sweep area may be swept by the beam 122 using a sweep path which is finer (in the case of a smaller sweep area) or coarser (in the case of a larger sweep area), in the sense that the paths traversed by the beam 122 will have closer or more distant spacing. The sweep path preferably takes the same form as in the prior sweep, i.e., it preferably uses the same sinuous, zig-zagging, spiral, etc. path which is merely compressed or enlarged in scale to cover much of the area of the new sweep area. During the new sweep, the beam alignment control system 310 again monitors the control parameters versus the alignment criteria to seek the location(s) which optimally indicate the presence of the apex of the specimen 104. Once the new sweep is completed, the sweep area is again redefined (shrunk or expanded) and swept with the control parameters being monitored versus the alignment criteria. The process continuously repeats in this manner, with the sweep area being iteratively shrunk about the home (optimal) location(s) until the alignment criteria are met to some predefined level of accuracy. Once this occurs—for example, once the control parameters of an identified home location do not significantly change between subsequent sweeps—the sweeping may be halted, and it can be assumed that the identified home location corresponds to the apex of the specimen 104.

The foregoing process is schematically illustrated in FIGS. 5a-5c. In FIG. 5a, the area 502 is concentrically situated about the apex of the specimen 104 (the location of which is unknown to the beam alignment control system 310). The beam alignment control system 310 defines an arbitrary location 504 about which the sweep area is defined, and further defines the sweep path 506, which in this case is defined as an array of adjacent straight lines/sweeps distributed across the sweep area. The sweep path 506 is traversed by the beam 122, and the control parameters collected during the sweep are measured versus the alignment criteria. (It should be understood that while the sweep path 506 is illustrated as a continuous line, it in fact consists of a series of discrete sample points, each being a location at which a laser pulse from the beam 122 is received.) The locations along the sweep path 506 within the area 502 meet the alignment criteria, and are this identified as optimal locations. A new sweep path center 508 (a home location) is therefore defined within the area 502 (FIG. 5b). The sweep area is then shrunk about the new sweep path center 508, and a finer sweep path 510 is defined and swept to identify a new home location (not shown). Subsequent sweeps are then performed to identify subsequent home locations, with each successive sweep being centered about the prior home location, until the alignment criteria are met to some desired degree of accuracy, indicating that the home location specifies the apex of the specimen 104.

In the prototypical atom probe 100 of FIG. 1b, where a 0.02 mm beam 122 is used, it typically takes numerous iterations to "home in" on the apex of the specimen 104. Smaller beams may require more iterations. Regardless of how many iterations are needed, the fine beam alignment process continuously follows the steps of locating the home location and rescaling the sweep area about the home location.

Numerous variations of the foregoing fine beam alignment process are possible. As one example, the beam alignment control system 310 could increase the sampling rate along the sweep path if the control parameters are converging on the alignment criteria, and can decrease the sampling rate if divergence occurs. It is also possible that the sweep area and/or sweep path might be immediately redefined once divergence is noted, so that the sweep area is immediately redefined about the area of convergence. Additionally, the sweep areas and sweep paths may take a wide variety of forms, and they need not take identical form from one sweep to the next; for example, one sweep might take the form of a straight line along an X axis, and the next sweep might take the form of a straight line along a Y axis defined about the home location in the prior sweep. It is also possible that the process might occur semiautomatically; for example, a plot of the control parameters might be displayed to the user, who would then have the opportunity to manually define a new home location for the next sweep.

Once fine alignment has been achieved, the laser atom probe 100 may begin data acquisition: the specimen 104 and detector 106 may each be charged to levels conducive to ionization of the specimen 104, and the laser 116 may be pulsed to add sufficient energy that ionization occurs. Since the beam 122 of the laser 116 may drift over time, the foregoing beam fine alignment process may periodically be repeated during data acquisition, perhaps after a certain number of data acquisition cycles occur, and/or after certain parameters (such as evaporation rates, mass resolution, etc.) appear to indicate that the beam 122 is no longer centered on the desired area of the specimen 104. Data acquisition need not be ceased during such fine alignment, since the data obtained from data acquisition may be used to generate many of the control parameters. Stated differently, data acquisition from the atom probe 100 may proceed in standard fashion, with the acquired data being monitored versus alignment criteria to verify whether the beam 122 is still directed at the apex of the specimen 104, and if the alignment criteria are not met, sweep areas may be defined and sweeping may be performed to re-locate the apex of the specimen 104.

Preferred versions of the laser atom probe 100 are shown in the drawings and described above merely to illustrate possible features of the laser atom probe 100 and the varying ways in which these features may be combined. Modified versions of the laser atom probe 100 are also considered to be within the scope of the invention. Following is an exemplary list of such modifications.

First, it is notable that a wide variety of operational modes are possible for the atom probe 100 to induce evaporation of the specimen, with any one or more of the specimen mount 102, counter electrode 108, and laser 116 providing energy to the specimen 104 in constant or pulsed fashion. The laser 116 is preferably pulsed since the narrow pulse widths achievable with a laser 116 are useful to more precisely specify ion departure times (and thus lead to better mass resolution), but steady operation of the laser 116, with pulsing of other components (to provide the overvoltage necessary for ionization), is possible. The use of a pulsing laser 116 with an overvoltage pulse applied to either or both of the counter electrode 108 and/or specimen mount 102 can be beneficial with some types of specimens 104 since this may allow the specimen 104 to remain at a lower boost voltage (and thus a lower field and lower mechanical stress) for the time between pulses, thereby improving the survival of delicate specimens 104 and simultaneously reducing spurious ionization events between pulses (which effectively results in lost data).

Second, apart from laser and electron beams 122, other beams bearing energies at different ranges of the electromagnetic spectrum might be used. Similarly, other forms of energy might be used to impart the boost (non-pulsed) energy, such as microwaves.

Third, some of the arrangements and methodologies described above might be implemented in a version of the atom probe 100 wherein the counter electrode 108 is omitted (or in a version of the atom probe 100 wherein a counter electrode 108 is included, but the beam 122 is not directed through the counter electrode 108). In either case, the aforementioned methods for coarse alignment of the beam 122 through the counter electrode 108 do not apply. Other methods of coarse alignment (followed by fine alignment) might then be used, though they may require more time and effort.

Figure 6A:
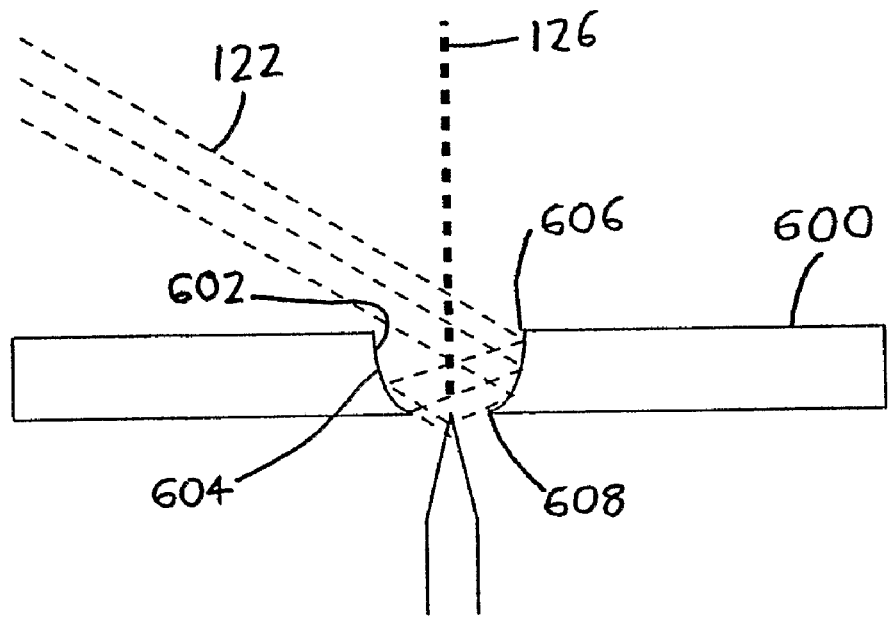
FIGS. 6a-6b schematically illustrate an alternative counter electrode 600 having a concentrating aperture 602 for concentrating energy (whether from the laser beam 122 or from a supplemental energy source 610) directed toward the specimen 104.
Figure 6B:
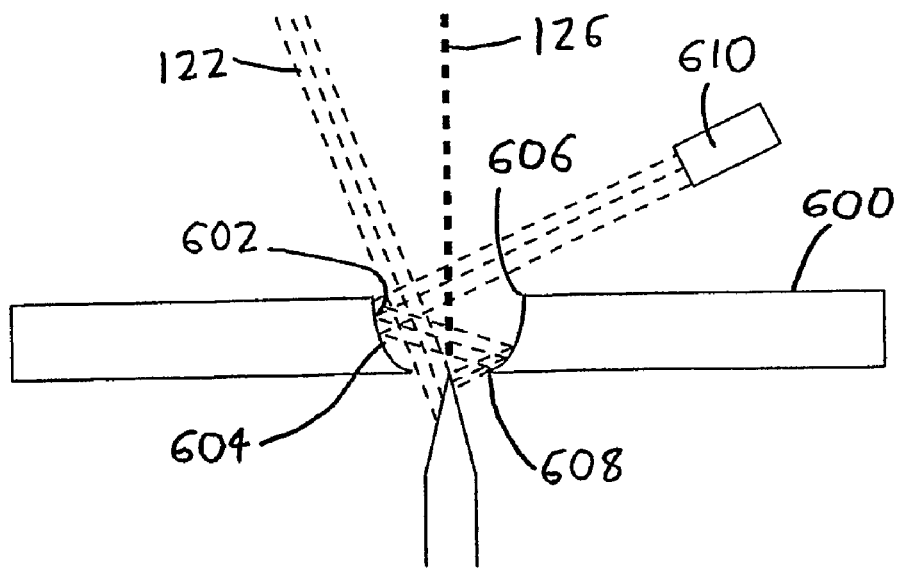

Fourth, it is emphasized that the counter electrode 108 may take a wide variety of sizes and configurations, including configurations which are not conventional to prior atom probes. An example is illustrated in FIGS. 6a and 6b. In FIG. 6a, an alternative to the counter electrode 108 of FIGS. 1a-1b is depicted, with the alternative counter electrode 600 providing certain additional and advantageous features over the basic counter electrode 108. Here, the counter electrode 600 has a converging aperture 602 which is configured such that radiation incident on its aperture walls 604 is reflected away from the aperture plane 606, i.e., away from the larger entry of the aperture 602, and toward the smaller aperture exit 608, whereby incident radiation is thereby collected and concentrated to higher intensity at the aperture exit 608. The configuration of the concentrating aperture 602 may take a variety of shapes, and such shapes may need to be chosen to provide optimal concentration for a given angle between the laser beam 122 and the ion travel axis 126 (i.e., for a given incidence angle). Information regarding concentrator design can be found, for example, in the field of solar energy, where concentrators are commonly used to collect sunlight. Other prior concentrators, and discussions of considerations relevant to concentrator design, can be found in (for example) U.S. Pat. No. 5,572,355 to Cotton et al.; U.S. Pat. No. 5,604,607 to Mirzaoft; U.S. Pat. No. 5,952,645 to Wang et al.; U.S. Pat. No. 5,978,407 to Chang et al.; and U.S. Pat. No. 6,704,341 to Chang, as well as in patents cited in (and citing to) these patents. Other useful references are R. N. Wilson, Reflecting Telescope Optics: Basic Design Theory and Its Historical Development, Springer-Verlag (1996) (for optical concentrators) and T. Wilhein, D. Hambach, B. Niemann, M. Berglund, L. Rymell, and H. M. Hertz, Off-axis reflecting soneplate for quantitative soft x-ray source characterization, Appl. Phys. Lett. 71, 190 (1997) (for concentrators for non-optical radiation).

The concentrating aperture 602 can provide several advantages. First, as implied by the arrangement depicted in FIG. 6a, the counter electrode 600 can accommodate a larger incidence angle, since the beam 122 need not necessarily directly impinge on the specimen 104, and can instead merely impinge on the aperture walls 604 to be directed onto the specimen 104 (which is situated immediately at the aperture exit 608 so as to receive the concentrated beam 122). A greater beam angle 122 might in some cases allow closer laser placement, or space-saving atom probe component layouts. Second, the counter electrode 600 can accommodate greater (and lower power) beam diameters, and can automatically concentrate beams of various diameters down to some desired diameter. Third, as implied by the prior two comments, the counter electrode 600 can accommodate a beam 122 which is not as precisely aligned with the specimen 104, since the aperture 602 can largely provide such alignment so long as the tip or other area of interest is itself aligned with the aperture exit 608.

FIG. 6b shows an arrangement similar to that of FIG. 6a, but here the laser beam 122 is directed through the aperture 602 and directly onto the area of interest on the specimen 104, as in the arrangements discussed previously. In this case, the concentrating aperture 602 is provided to receive and collect supplemental energy (supplied in pulsed or steady fashion) from one or more supplemental energy sources 610, with such energy being directed onto the specimen 104 for ionizing or other purposes. A supplemental energy source 610 could be a light source such as another laser, LED laser, LED, or a traditional lamp, whether in the visible or invisible portions of the spectrum, and its light can be beamed from a location distant from the electrode 600 or may be piped to the electrode 600 by a fiberoptic cable or other light guide. As an alternative, a supplemental energy source 610 could transmit radio, microwave, or other electromagnetic radiation. The energy supplied by the supplemental energy source 610 could be provided for purposes in addition to or other than ionization, such as for modifying the characteristics of a specimen 104. As an example, a silicon-based specimen 104 might experience a change in conductivity if illuminated by a supplemental energy source 610 emitting infrared light (with such a conductivity perhaps allowing a lower boost voltage to be supplied to the specimen 104). Arrangements are also possible wherein only a non-laser and/or non-ionizing supplemental energy source 610 directs energy through the aperture 602, with no laser being included (i.e., with the concentrating electrode 600 being used in conjunction with a non-laser supplemental energy source 610 in a more conventional atom probe arrangement), or wherein the concentrating electrode 600 and supplemental energy source 610 are used in conjunction with a laser beam which is not directed through the aperture 602.

Fifth, other arrangements are possible which yield effects similar to that of the concentrating electrode 600 (with or without a supplemental energy source). As an example, a single laser beam could be split into two or more beams, each of which are directed toward the specimen at a different angle, with the beams perhaps being distributed for more even illumination of the tip or other area of interest; and/or with one or more beams being adjusted to a different wavelength (as by use of the aforementioned nonlinear crystals); and/or with one or more of the beams being directed through the electrode aperture, with others being directed onto the specimens from outside the aperture.

Sixth, many other atom probe features known in the field but not noted in the foregoing discussion may be used with the atom probe 100. As an example, a recessed viewport 120 (a viewport 120 situated at the end of a viewing tube 118 extending into the vacuum chamber 114), as described in U.S. Pat. No 6,762,415 to Strait, may be utilized to reduce the distance between the laser 116 and specimen 104 to reduce alignment burdens.

The invention is not intended to be limited to the preferred versions described above, but rather is intended to be limited only by the claims set out below. Thus, the invention encompasses all different versions that fall literally or equivalently within the scope of these claims.

Bibliography

1. U.S. Pat. No. 5,061,850 to Kelly et al. ("High mass resolution local-electrode atom probe")
2. U.S. Pat. No. 5,440,124 to Kelly et al. ("High-repetition rate position sensitive atom probe")
3. U.S. Pat. No. 6,576,900 to Kelly et al. ("Methods of sampling specimens for microanalysis")
4. U.S. Pat. No. 6,580,069 to Cerezo ("Atom probe")
5. U.S. Pat. No. 6,700,121 to Kelly et al. ("Methods of sampling specimens for microanalysis")
6. U.S. Pat. No. 6,762,415 to Strait ("Vacuum chamber with recessed viewing tube and imaging device situated therein")
7. International Publication WO 99/14793
8. International Publication WO 87/00682
9. Cerezo, A. et al., J. Phys. (Orsay) C9 (1984) p. 315.
10. Cerezo, A., C. R. M. Grovenor and G. D. W. Smith. "Pulsed laser atom probe analysis of semiconductor materials." Journal of Microscopy v 141, pt.2 (Feb. 1986): 155-170.
11. Drachsel, W., Nishigaki, S., and Block, J. H., "Photon-Induced Field Ionization Mass Spectroscopy." Int. J. Mass Spectrom. and Ion Phys. Vol. 32 (1980): 333-343.
12. Kellogg, G. L., and T. T. Tsong. "Pulsed-laser atom-probe field-ion microscopy." Journal of Applied Physics 51 (2) (1980): 1184-1193.
13. Kelly, T. F., Zreiba, N. A., Howell, B. D., and Bradley, F. J., "Energy Deposition and Heat Transfer in a Pulse-Heated Field Emission Tip at High Repetition Rates." Surface Science, vol. 246 (1991): 377-385.
14. Kelly, T. F. , Camus, P. P., Larson, D. J., Holman, L. M., and Bajikar, S. S., Ultramicroscopy 62:29-42 (1996).
15. Kelly, T. F. and Larson, D. J., "Local Electrode Atom Probes." Materials Characterization 44, 59-85 (2000).
16. Liu, J., and T. T. Tsong. "Kinetic Energy and Mass Analysis of Carbon Cluster Ions in Pulsed-Laser-Stimulated Field Evaporation." Physical Review (B) 38 (12) (1988): 8490-8493.
17. Liu, J., C. Wu, and T. T. Tsong. "Measurement of the atomic site specific binding energy of surface atoms of metals and alloys." Surface Science 246 (1991) 157-162.
18. Miller, M. K., A. Cerezo, M. G. Hetherington, and G. D. W. Smith. "Atom Probe Field Ion Microscopy." Oxford Science Publications, 1996.
19. Tsong, T. T., Photon stimulated field ionization, J. Chem. Phys. 65, 2469 (1976).
20. Tsong, T. T., S. B. McLane, and T. J. Kinkus. "Pulsed-laser time-of-flight atom-probe field ion microscope." Review of Scientific Instruments 53(9), September 1982.
21. Tsong, T. T. "Pulsed-Laser-Stimulated Field Ion Emission from Metal and Semiconductor Surfaces: A Time-of-Flight Study of the Formation of Atomic, Molecular, and Cluster Ions." Physical Review (B) 30 (9) (1984): 4946-4961.

The invention claimed is:

1. An automated process for aligning an energy beam to a specimen in an atom probe, the atom probe having a specimen mount spaced from a detector, the process comprising the steps of:
   a. sweeping an energy beam in one or more dimensions over a sweep area, the sweep area being on or near the specimen;
   b. during the sweep, monitoring one or more parameters indicative of the interaction between the energy beam and the specimen;
   c. defining a subset of the sweep where the monitored parameters meet predefined alignment criteria;
   d. repeating the process from step a. above after reducing the sweep area, wherein the reduced sweep area encompasses at least the subset of step c.

2. The process of claim 1 further comprising the step of halting the sweeping once the subset of the sweep meets the predefined alignment criteria to a predefined level of accuracy.

3. The process of claim 2 further comprising the subsequent steps of:
   a. directing the energy beam toward at least a portion of the subset; and
   b. pulsing the energy beam with an intensity sufficient to induce ionization on the subset.

4. The process of claim 1 wherein the subset is a home location at which the parameters monitored during the sweep best meet desired alignment criteria.

5. The process of claim 4 wherein any second and subsequent sweeps have sweep areas with locations dependent upon the location of the prior sweep area.

6. The process of claim 4 wherein any second and subsequent sweeps have sweep areas centered about the subset defined in the prior sweep.

7. The process of claim 1 wherein the energy beam is a laser beam.

8. The process of claim 1 wherein the energy beam is directed through a counter electrode during sweeping, the counter electrode being interposed between the specimen and the detector.

9. The process of claim 1 wherein one of the monitored parameters is the collection rate of any ions detected by the detector.

10. The process of claim 1 wherein one of the monitored parameters is any voltage applied to the specimen mount necessary to attain a desired ion collection rate at the detector.

11. The process of claim 1 wherein one of the monitored parameters is the mass resolution of any ions detected by the detector.

12. The process of claim 1 wherein one of the monitored parameters is the reflection of the energy beam.

13. The process of claim 1 wherein one of the monitored parameters is the diffraction of the energy beam.

14. An automated process for aligning an energy beam to a specimen in an atom probe, the atom probe having a specimen mount spaced from a detector, the process comprising the steps of:

a. sweeping an energy beam in one or more dimensions over a sweep area, the sweep area being on or near the specimen;
b. during the sweep, monitoring one or more parameters indicative of the interaction between the energy beam and the specimen;
c. identifying one or more locations along the sweep at which the monitored parameters meet predefined alignment criteria;
d. repeating the process from step a. above after:
   (1) reducing the sweep area to encompass at least one of any locations identified in step c.; or
   (2) increasing the sweep area if no location is identified in step c.

15. The process of claim 14 further comprising the step of halting the sweeping once a location is identified in step c. which meets the desired alignment criteria to a predetermined level of accuracy.

16. The process of claim 15 further comprising the subsequent steps of:
   a. directing the energy beam at the location which meets the desired alignment criteria to a predetermined level of accuracy; and
   b. pulsing the energy beam with an intensity sufficient to induce ionization at the location.

17. The process of claim 14 wherein any sweeps having reduced sweep areas have their sweep areas set at locations dependent upon at least one of the locations along the prior sweep at which the monitored parameters have met the predefined alignment criteria.

18. The process of claim 14 wherein any sweeps having reduced sweep areas have their sweep areas centered about at least one of the locations along the prior sweep at which the monitored parameters have met the predefined alignment criteria.

19. The process of claim 14 wherein the energy beam is a laser beam.

20. The process of claim 14 wherein the energy beam is directed through a counter electrode during sweeping, the counter electrode being interposed between the specimen and the detector.

21. The process of claim 14 wherein one of the monitored parameters is the collection rate of any ions detected by the detector.

22. The process of claim 14 wherein one of the monitored parameters is any voltage applied to the specimen mount necessary to attain a desired ion collection rate at the detector.

23. The process of claim 14 wherein one of the monitored parameters is the mass resolution of any ions detected by the detector.

24. The process of claim 14 wherein one of the monitored parameters is the reflection of the energy beam.

25. The process of claim 14 wherein one of the monitored parameters is the diffraction of the energy beam.

26. An automated process for aligning an energy beam to a specimen in an atom probe, the atom probe having a specimen mount spaced from a detector, the process comprising the steps of:
   a. directing an energy beam toward the specimen mount;
   b. sweeping the energy beam in one or more dimensions over a sweep area of predefined size, while monitoring one or more parameters indicative of the interaction between the energy beam and the specimen;
   c. defining a home location along the sweep at which the monitored parameters best meet desired alignment criteria;
   d. repeating the process from step b. above after:
      (1) resizing the sweep area, and
      (2) starting the sweep at or about the home location.

27. The process of claim 26 further comprising the step of halting the sweeping once the home location meets the desired alignment criteria to a predetermined level of accuracy.

28. The process of claim 27 further comprising the subsequent steps of:
   a. directing the energy beam at the home location; and
   b. pulsing the energy beam with an intensity sufficient to induce ionization on the specimen.

29. The process of claim 26:
   a. further comprising the step of monitoring the degree of change in at least one of the monitored parameters during each sweep; and
   b. wherein if the degree of change does not meet a predetermined threshold, the step of resizing the sweep area comprises enlarging the sweep area.

30. The process of claim 26:
   a. further comprising the step of monitoring the degree of change in at least one of the monitored parameters during each sweep; and
   b. wherein if the degree of change:
      (1) meets a predetermined threshold, the step of resizing the sweep area comprises reducing the sweep area;
      (2) does not meet a predetermined threshold, the step of resizing the sweep area comprises enlarging the sweep area.

31. The process of claim 26 wherein each sweep occurs in directions different from the directions of the prior sweep.

32. The process of claim 26 wherein the second and any subsequent sweeps have sweep areas with locations set in dependence upon the home location of the prior sweep.

33. The process of claim 26 wherein the second and any subsequent sweeps have sweep areas centered about the home location of the prior sweep.

34. The process of claim 26 wherein the energy beam is a laser beam.

35. The process of claim 26 wherein the energy beam is directed through a counter electrode during sweeping, the counter electrode being interposed between the specimen and the detector.

36. The process of claim 26 wherein one of the monitored parameters is the collection rate of any ions detected by the detector.

37. The process of claim 26 wherein one of the monitored parameters is any voltage applied to the specimen mount necessary to attain a desired ion collection rate at the detector.

38. The process of claim 26 wherein one of the monitored parameters is the mass resolution of any ions detected by the detector.

39. The process of claim 26 wherein one of the monitored parameters is the reflection of the energy beam.

40. The process of claim 26 wherein one of the monitored parameters is the diffraction of the energy beam.

41. An automated process for aligning an energy beam to a specimen in an atom probe, the atom probe having a specimen mount spaced from a detector, the process comprising the steps of:
   a. sweeping a laser beam in one or more dimensions over a sweep area, the sweep area being on or near the specimen;
   b. monitoring one or more of the following parameters during the sweep:
      (1) the collection rate of any ions detected by the detector;

(2) the mass resolution of any ions detected by the detector;
(3) any voltage applied to the specimen mount;
(4) any reflected portions of the laser beam; and
(5) any scattered portions of the laser beam;
c. identifying one or more locations along the sweep at which the monitored parameters meet predefined alignment criteria;
d. repeating the process from step a. above after:
(1) reducing the sweep area to encompass at least one of any locations identified in step c.; or
(2) increasing the sweep area if no location is identified in step c.

42. The process of claim 41 wherein the energy beam is directed through a counter electrode during sweeping, the counter electrode being interposed between the specimen and the detector.

* * * * *

UNITED STATES PATENT AND TRADEMARK OFFICE
CERTIFICATE OF CORRECTION

PATENT NO.       : 7,652,269 B2                                    Page 1 of 1
APPLICATION NO. : 11/597080
DATED            : January 26, 2010
INVENTOR(S)      : Bunton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 642 days.

Signed and Sealed this

Twenty-third Day of November, 2010

David J. Kappos
*Director of the United States Patent and Trademark Office*